United States Patent
Beek et al.

(10) Patent No.: US 9,649,451 B2
(45) Date of Patent: May 16, 2017

(54) INJECTION DEVICE WITH INTEGRATED NEEDLE SHIELD

(71) Applicant: Novo Nordisk A/S, Bagsvaerd (DK)

(72) Inventors: Willem van der Beek, Virum (DK); Roger Harrington, Skaevinge (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/646,144

(22) PCT Filed: Nov. 25, 2013

(86) PCT No.: PCT/EP2013/074611
§ 371 (c)(1),
(2) Date: May 20, 2015

(87) PCT Pub. No.: WO2014/082959
PCT Pub. Date: Jun. 5, 2014

(65) Prior Publication Data
US 2015/0320939 A1     Nov. 12, 2015

Related U.S. Application Data

(60) Provisional application No. 61/733,065, filed on Dec. 4, 2012.

(30) Foreign Application Priority Data

Nov. 29, 2012   (EP) .................................... 12194739

(51) Int. Cl.
*A61M 5/32*     (2006.01)
*A61M 5/315*    (2006.01)
*A61M 5/20*     (2006.01)

(52) U.S. Cl.
CPC ............ *A61M 5/3234* (2013.01); *A61M 5/20* (2013.01); *A61M 5/2033* (2013.01);
(Continued)

(58) Field of Classification Search
CPC .. A61M 2005/3247; A61M 2005/3238; A61M 5/3257; A61M 2005/208;
(Continued)

(56) References Cited

U.S. PATENT DOCUMENTS 5,695,474 A    12/1997  Daugherty
7,112,187 B2    9/2006  Karlsson
(Continued)

FOREIGN PATENT DOCUMENTS

EP      338806 A2    10/1989
EP     2399628 A1    12/2011
(Continued)

*Primary Examiner* — Edelmira Bosques
*Assistant Examiner* — Nawal Boufrou
(74) *Attorney, Agent, or Firm* — Wesley Nicolas

(57) ABSTRACT

The invention relates to injection device, which device comprises an outer housing (1), a syringe body (10) and a needle shield (30). Both the syringe body (10) and the needle shield (30) are telescopically movable mounted to the housing (1) such that the needle shield (30) is movable relatively to the housing (1) between a first position and a second position, and the syringe body (10) is movable in relation to the housing (1) between an extended position and a retracted position.

10 Claims, 3 Drawing Sheets

(52) U.S. Cl.
CPC ...... *A61M 5/31525* (2013.01); *A61M 5/3205* (2013.01); *A61M 5/326* (2013.01); *A61M 5/3219* (2013.01); *A61M 5/3243* (2013.01); *A61M 5/3257* (2013.01); *A61M 5/3269* (2013.01); *A61M 5/3275* (2013.01); *A61M 2005/208* (2013.01); *A61M 2005/3267* (2013.01)

(58) Field of Classification Search
CPC ............ A61M 2005/3267; A61M 5/20; A61M 5/2033; A61M 5/31525; A61M 5/3234; A61M 5/3243; A61M 5/326; A61M 5/3205; A61M 2005/206; A61M 1/1037; A61M 1/1063; A61M 1/285
See application file for complete search history.

(56) References Cited

U.S. PATENT DOCUMENTS

| | | | |
|---|---|---|---|
| 2002/0026146 | A1 | 2/2002 | Jansen et al. |
| 2006/0178630 | A1* | 8/2006 | Bostrom ............. A61M 5/2066 604/135 |
| 2010/0036325 | A1 | 2/2010 | Liversidge |
| 2013/0237905 | A1* | 9/2013 | Holmqvist ........ A61M 5/31525 604/89 |

FOREIGN PATENT DOCUMENTS

| | | | |
|---|---|---|---|
| WO | 2009023893 | A1 | 2/2009 |
| WO | 2010026414 | A1 | 3/2010 |
| WO | 2012045350 | A1 | 4/2012 |
| WO | 2012067583 | A1 | 5/2012 |

\* cited by examiner

INJECTION DEVICE WITH INTEGRATED NEEDLE SHIELD

CROSS-REFERNCE TO RELATED APPLICATIONS

This application is a 35 U.S.C. §371 National Stage of International Application PCT/EP2013/074611(published as WO2014/082959), filed Nov. 25, 2013, which claims priority to European Patent Application 12194739.4, filed Nov. 29, 2012; this application claims priority under 35 U.S.C. §119 to U.S. Provisional Application 61/733,065; filed Dec. 4, 2012.

THE TECHNICAL FIELD OF THE INVENTION

The invention relates to an injection device for injecting multiple doses of a liquid drug via an attachable injection needle which is concealed during injection. The injection device has an outer housing carrying a slidable syringe body and a slidable needle shield covering the injection needle and which shield is preferably used to trigger and release an automatic spring mechanism performing the injection.

DESCRIPTION OF RELATED ART

WO 2012/067583 discloses a so-called single-shot injection device i.e. an injection device for performing one single injection of a predetermined dose size. When mixing the drug in the cartridge prior to use an outer element is rotated which then moves the syringe body proximally whereby the injection needle becomes covered by a telescopic movable shield. During injection the shield is pressed against the skin of a user and thus moved proximally. The predetermined dose is expelled when the user presses an injection button. When removing the shield from the skin of the user a spring urges the shield in a distal direction into a locked position. The syringe body and the shield are thus only movable once where after the injection device is discarded. It is hence not possible to change the injection needle and perform a second injection.

An automatic torsion spring driven injection device for multiple and settable injections are disclosed in EP 338,806. In one embodiment, the injection needle is covered by a telescopically movable needle shield. When the shield is pressed against the skin of a user, a compression spring drives the body of the pen forward such that the tip of the needle cannula penetrates the skin of the user, and a torsion spring is released to perform an injection of the liquid drug contained in the injection device. However, exchanging the injection needle is troublesome as the user needs to remove the needle shield in order to gain access to the injection needle.

A different spring driven pen-shaped injection device having a shielded injection needle is known from U.S. Pat. No. 7,112,187. The injection device disclosed is an automatic spring-driven injection in which an actuation spring, in the form of a compression spring, provided inside the housing thrusts the piston rod forward during injection. An important characteristic of such automatic injection device is that no elements move out from the injection device during dose setting. Thus, the injection device has a constant length during operation. This particular injection device has a mode selector which is rotated to select one out of three different modes. In one mode the shield is locked and in a different mode the shield is unlocked. In the unlocked position, the shield can be moved axially between an extended and a retracted position. In the retracted position a user has access to the distal end of the injection device and is thus able to attach or remove an injection needle. Further, the mode selector can be rotated to an injection position, in which position the set dose is released when the shield is moved to its retracted position during injection.

For automatic spring driven injection devices for multiple injections of settable doses in which the triggering of the injection is made by the backward movement of the needle shield the changing of the sterile injection needle is a particular challenge. In order to repeatedly gain access to the needle interface on the injection device, the needle shield needs to be removed such that the user can rotate or twist the needle hub onto the interface in order to couple or decouple the injection needle. However, when performing the injection, the needle shield must trigger the release of the dose when the distal part of the needle cannula is penetrated into the body.

In EP 338,806 this is solved by simply removing the needle shield during changing of the injection needle whereas in U.S. Pat. No. 7,112,187 it is done by a complicated mechanism involving a mode selector. However, in both examples it is difficult to explain the user how to handle the injection device as the user has to perform many different steps and remember which steps in the sequence of executing the injection he or she has fulfilled.

DESCRIPTION OF THE INVENTION

Injection devices for multiple dosing usually require changeability of the injection needle between the multiple injections in order to have a sterile injection needle mounted for each new injection. The changing of the injection needle between injections is especially troublesome in injection devices having a shielded injection needle and wherein the needle shield triggers the injection.

It is therefore an object of the present invention to provide a shield triggered spring driven injection device for multiple automatic injections of doses of a drug, wherein the changing of the hidden injection needle is very simple and which do not require any wider explanation to the user, but where the working of the injection device and the needle change mechanism is self-explanatory.

The invention is defined in claim 1. Accordingly, in one aspect of the present invention, the injection device is preferably shield triggered and comprises three main components;

An outer housing,
A needle shield, and
A syringe body.

The outer housing is usually held in the hand of the user during operation.

The syringe body holds and secures the cartridge containing the liquid drug. The syringe body further has a dose setting mechanism for setting the size of the dose to be injected and a dose injection mechanism for ejecting the set dose.

The needle shield covers the injection needle during injection and is preferably also used to release the set dose e.g. as disclosed in PCT/EP2013/063250.

The needle shield and the syringe body are both telescopically moveable relatively to the housing and the syringe body carries an injection needle covered by the needle shield.

In a first situation of use when getting ready to inject, the user presses the syringe body in the distal direction such that the needle interface provided on the syringe body extends beyond the needle shield enabling the user to exchange the injection needle. The forward pressure on the syringe body is simply performed by the user pressing a finger against the proximal end of the syringe body. Once the user removes his pressure from the syringe body a spring means or the like urges the syringe body in the proximal direction thus hoisting the injection needle into coverage by the needle shield. The syringe body is thus able to move between a retracted position and an extended position, the default position being the retracted position.

When an injection needle has been mounted and the syringe body is in its retracted position, the user is ready to perform an injection. This is done by pressing the needle shield against the surface of the skin of the user thus moving the needle shield from its first position to its second position. This causes the needle shield to slide in the proximal direction allowing the injection needle to penetrate the skin of the user and at the same time releasing the injection mechanism to expel a set dose of the drug contained in the syringe body. The needle shield is thus able to operate between a first position and a second position, the first position being the default position.

By being shield triggered is thus meant that the set dose is released preferably to be automatically injected when the shield is in the second position or when the shield is approaching the second position, however manual release of the set dose when the needle shield is in the second position could also be a foreseen.

Spring means are provided to bias the needle shield to its first position and/or the syringe body to its retracted position. These spring means are preferably helically wounded springs provided in specific positions urging the syringe body proximally and the needle shield distally.

The spring means provided can be either compression springs or tension springs (or a combination thereof). There can be provided a number of different springs, however one and the same spring can be utilized for both purposes.

In a preferred embodiment one single—preferably helically wounded—tension spring can be encompassed between the needle shield and the syringe body which spring is stretched when the needle shield is moved proximally or when the syringe body is moved distally. The stretching of the tension spring results in the spring applying a force urging the needle shield in the distal direction and the syringe body in the proximal direction, as a tension spring when stretched provides an axial force opposite the direction in which it is stretched.

By only using one single spring, the mechanics of the injection device can be simplified and the production cost lowered.

A plurality of stopping surfaces is provided. In one embodiment the outer housing defines a distal stopping surface abutting a first stopping surface on the needle shield when the needle shield is in its first position thereby limiting the axial distal movement of the needle shield in the distal direction.

Further the outer housing defines a proximal stopping surface abutting a second stopping surface on the needle shield when the needle shield is in its second position thereby limiting the axial movement of the needle shield in the proximal direction.

The axial movement of the syringe body relatively to the housing can be regulated by a tongue and groove engagement. In one embodiment a longitudinal tongue on the syringe body defines a distal end abutting an end of a corresponding groove in the housing when the syringe body is in its extended position. This longitudinal tongue further defines a proximal end abutting the corresponding groove of the housing when the syringe body is in its retracted position.

The needle shield can be provided with a proximal extension which carries the stops. The proximal extension can e.g. carry the first stopping surface and the second stopping surface provided on the needle shield.

The proximal extension is preferably inrotatable guided in a guiding arrangement of the syringe body. Alternatively, the extension can be a simple prolongation of the needle shield itself such that the extension stretches all 360 degrees around the syringe body and slides on the outside surface of the syringe body.

In one example, the spring is at one end connected to the shield e.g. by being connected to the proximal extension of the shield. The opposite end of the spring is secured to the syringe body e.g. by being connected to a ring-shaped element secured to the syringe body. Since the spring is a tension spring operating between the needle shield and the syringe body these two parts are always urged in opposite axial directions. In the example the spring is a tension spring urging the needle shield in the distal direction into the first position and urging the syringe body in the proximal direction into the retracted position.

The needle shield is designed such that the shield in, or on its way towards, the second position activates the automatic dose injection mechanism to inject the set dose. The triggering mechanism is however designed such that it is not released when the syringe body is moved forward to exchange the injection needle but only released when a the shield is slided into the second position.

DEFINITIONS

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the back-end of an injection needle. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Further the term "injection needle" defines a piercing member adapted to penetrate the skin of a subject for the purpose of delivering or removing a liquid. For many pen systems, the needle cannula of the injection needle comprises a front part for penetrating the skin of the user and a back part for penetrating the septum of the cartridge thus creating a liquid flow between the interior of the cartridge and the subcutaneous layer of the user.

Using the term "Automatic" in conjunction with injection device means that, the injection device is able to perform the injection without the user of the injection device delivering the force needed to expel the drug during dosing. The force is typically delivered—automatically—by automatic means such as an electric motor or a spring. The spring is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on the injection device to release the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle.

Figure 1:
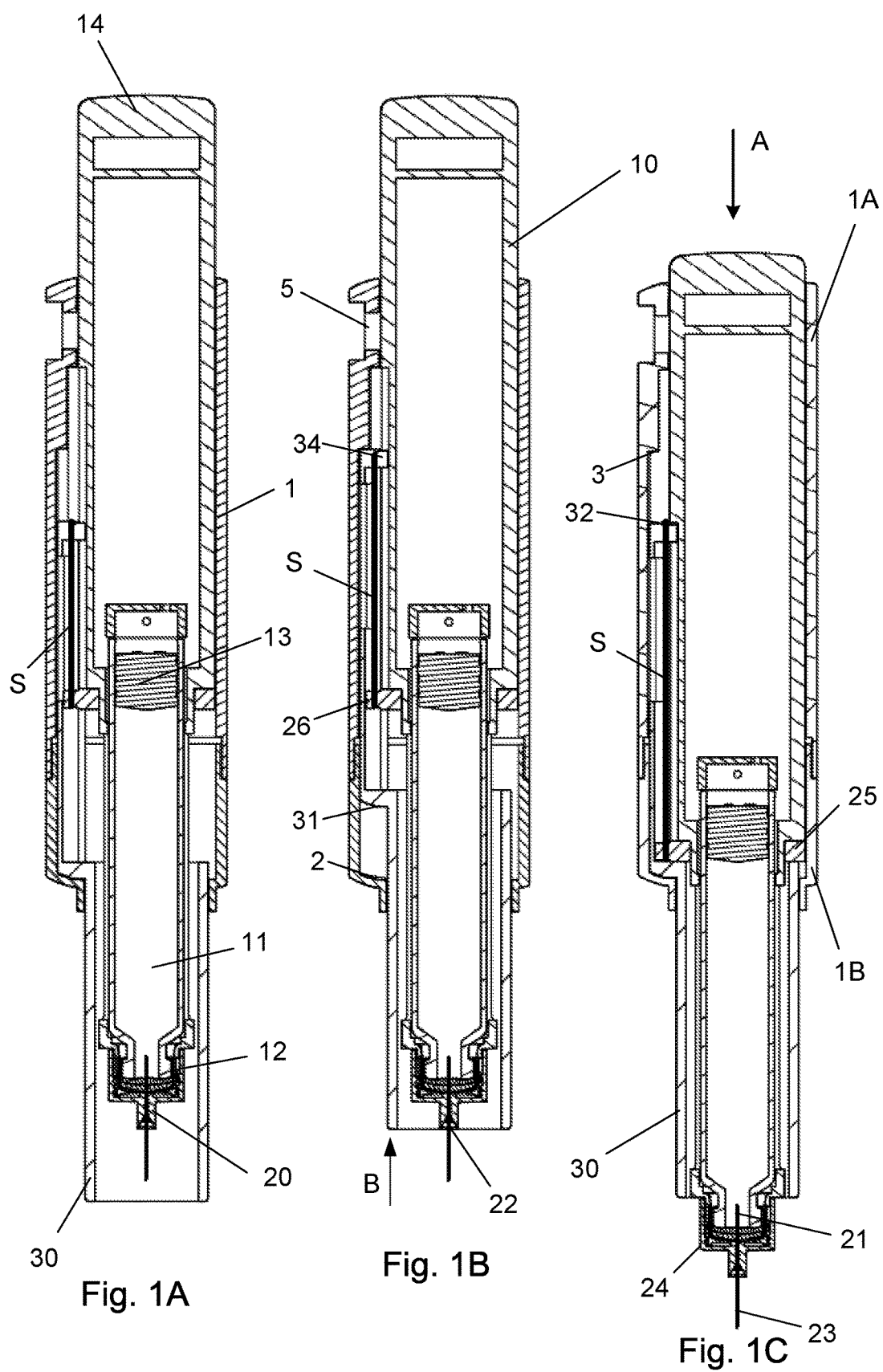
FIG. 1A-C show a cross sectional view of the injection device.

FIG. 1A to 1C discloses an injection device primarily comprises of four parts:

An outer housing 1, a syringe body 10, a needle shield 30 and a mountable injection needle 20.

The outer housing 1 is the outer part which a user holds in his hand and both the syringe body 10 and the needle shield 30 is mounted to the housing 1 in a telescopically movable manner.

The syringe body 10 holds a cartridge 11 and is distally provided with a needle receiving interface 12. A well-known pen needle 20 is mounted to the needle interfaces 12 such that a back-part 21 of the needle cannula 22 penetrates into the cartridge 11 and a front-part 23 points in the distal direction. The needle cannula 22 is secured in a hub 24 which has means mating with the needle interface 12

A piston 13 is provided inside the cartridge 11 which piston 13 is moved forward by a non-shown piston rod controlled by the dose injection mechanism. This forward movement forces a quantity of the drug to escape through the lumen of the needle cannula 20. The forward movement and thereby the size of the quantity expelled is controlled by the dose setting mechanism. The dose injection mechanism preferably comprises an automatic spring driven mechanism which is actuated by the needle shield 30.

The syringe body 10 is telescopically mounted in the housing 1 such that the syringe body 10 is movable between two extreme positions; a retracted position and an extended position.

The retracted position is the default position in which the syringe body 10 will rest when no pressure is applied to it. This retracted position is depictured in FIGS. 1A and 1B.

When a user wants to exchange the pen needle 20 he can apply a pressure to the proximal end 14 of the syringe body 10 (indicated by the arrow A in FIG. 1C) whereby the syringe body 10 moves axially forward to the extended position in which the entire needle interface 12 is outside the range of the needle shield 30 as depictured in FIG. 1C thus allowing the user to gain access to the needle interface 12 and to exchange the pen needle 20.

When a new pen needle 20 has been mounted and the proximal pressure (A) has been removed, the syringe body 10 will slide into its default position depictured in FIG. 1A. This is due to the force of the spring element S urging the syringe body 10 in the proximal direction relatively to the housing 1. (The spring element S is depicted as a straight line for simplicity but is preferably a helical wounded tension spring.)

The same spring element S or alternatively a second spring element urges the needle shield 30 in the distal direction to cover the needle cannula 22. When the needle shield 30 is pressed against the skin of a user (indicated by the arrow "B" in FIG. 1B), the needle shield 30 is moved proximally as disclosed in FIG. 1B. This proximal movement preferably releases the injection mechanism to perform an ejection of the drug.

This non-shown release mechanism is provided such that the proximal movement of the needle shield 30 activates the release, whereas the distal movement of the syringe body 10 do not activate the release.

Figure 2:
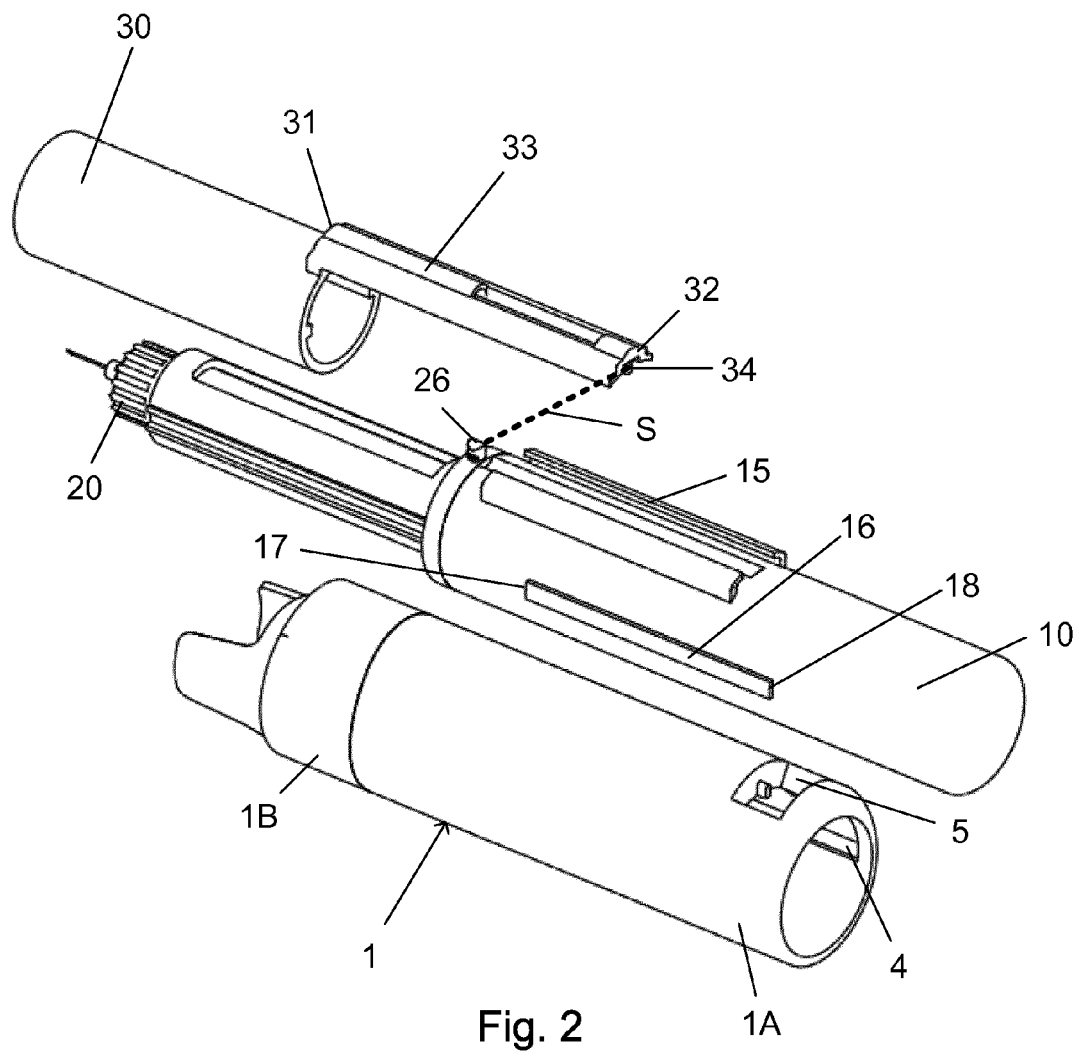
FIG. 2 show an exploded view of the main parts of the injection device.

FIG. 2 discloses the four parts; the outer housing 1, the syringe body 10, the mountable pen needle 20 and the needle shield 30. The internal relationship between these four parts are disclosed in FIG. 3

Figure 3:
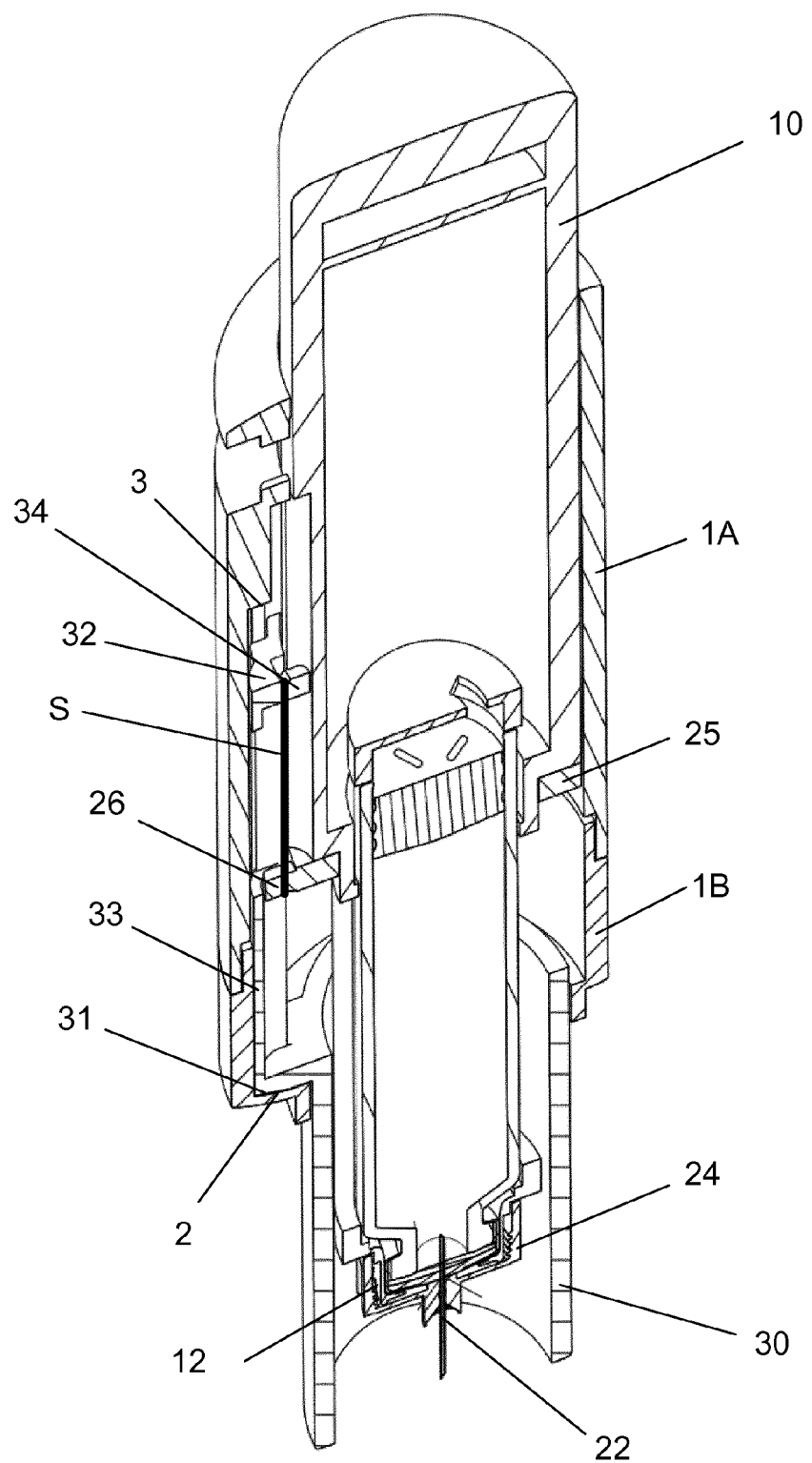
FIG. 3 show a view of the injection device in the default position of FIG. 1A.

The outer housing 1 is internally provided with a distal stopping surface 2 and a distal stopping surface 3 as disclosed in FIG. 3.

The needle shield 30 is provided with a proximal extension 33 which in operation are guided in a guiding arrangement 15 provided on the syringe body 10. This proximal extension 33 defines a first stopping surface 31 and a second stopping surface 32.

The proximal extension 33 on the needle shield 30 could alternatively be formed around 360 degrees thus fully surrounding the syringe body 10 in which case no separate guiding means is necessary as it is guided by on the external surface of the syringe body 10.

In the default position (FIG. 1A and FIG. 3), the first stopping surface 31 engages with the distal stopping surface 2 in the housing and when the needle shield 30 is moved to its second position (FIG. 1B), the second stopping surface 32 engages the proximal stopping surface 3 of the housing 1. Thus, the needle shield 30 is movable between the distal stopping surface 2 and the proximal stopping surface 3 defined in the outer housing 1.

Internally the housing 1 is provided with an axial groove 4 in which a longitudinal nut 16 provided on an external surface of the syringe body 10 is guided. This longitudinal nut 16 defines a distal end 17 and a proximal end 18, which again defines an axial operation range within which the syringe body 10 can move relatively to the housing 1.

The syringe body 10 is further equipped with a ring 25 which is secured to the syringe body and provided with an outwardly pointing protrusion 26. The spring element S is preferably provided between this outwardly pointing protrusion 26 on the ring 25 and an inwardly pointing protrusion 34 provided on the proximal extension 33 of the needle shield 30 as indicated by the broken line S in FIG. 2. This spring element S is preferably a tension spring which is stretched when the needle shield 30 is moved proximally or when the syringe body 10 is moved distally.

Further as disclosed in FIGS. 2 and 3, the outer housing 1 is made from two parts 1A, 1B which is connected preferably by a snap connection, by being glued together or by being welded together. The housing 1 is further provided with a window 5 through which the size of the set dose can be inspected. As the visual means showing the size of the dose is usually carried on a scale indicator being a part of the dose setting mechanism encapsulated in the syringe body 10, the syringe body 10 is preferably transparent or at least has a transparent area aligned with the window 5.

Some preferred embodiments have been shown in the foregoing, but it should be stressed that the invention is not limited to these, but may be embodied in other ways within the subject matter defined in the following claims. The relative axial movement of the needle shield could be designed in other ways than in the above example of the invention. E.g. by using a slider incorporated in the outer housing as an alternative to pushing the on the syringe body. Alternatively a twist mechanism could be provided such that a rotational movement is translated to an axial movement. Finally, the spring could be adapted such that gravity could perform the movement merely by tilting the injection device.

The invention claimed is:

1. An injection device for injecting multiple settable doses of a liquid drug via an attachable injection needle comprising;
   an outer housing,
   a syringe body which holds;
      a cartridge for the liquid drug,
      and
      a needle interface to which the injection needle is attachable,
   a needle shield telescopically and repeatable movable relatively to the housing between a first position and a second position;
      the first position being a position in which the attached injection needle is axially covered by the needle shield, and
      the second position being a position in which at least a part of the attached injection needle extends beyond the needle shield ready to perform an injection,
   wherein the syringe body is telescopically and repeatable movable in relation to the housing between a retracted position and an extended position;
      the retracted position being a position in which the needle interface is covered by the needle shield, and
      the extended position being a position in which the needle interface protrude beyond the needle shield thereby enabling a user to attach the injection needle to the needle interface, and
   the needle shield is urged toward the first position and the syringe body is urged towards the retracted position by one single tension spring structure encompassed between the needle shield and the syringe body.

2. An injection device for injecting multiple settable doses according to claim 1, wherein the outer housing defines a distal stopping surface abutting a first stopping surface on the needle shield when the needle shield is in its first position.

3. An injection device for injecting multiple settable doses according to claim 2, wherein the outer housing defines a proximal stopping surface abutting a second stopping surface on the needle shield when the needle shield is in its second position.

4. An injection device for injecting multiple settable doses according to claim 2, wherein the first stopping surface and the second stopping surface are provided on a proximal extension of the needle shield.

5. An injection device for injecting multiple settable doses according to claim 4, wherein the proximal extension is inrotatable guided in a guiding arrangement of the syringe body.

6. An injection device for injecting multiple settable doses according to claim 4, wherein the spring structure is encompassed between the proximal extension and the syringe body.

7. An injection device for injecting multiple settable doses according to claim 6, wherein the spring structure is encompassed between the proximal extension and a ring connected to the syringe body.

8. An injection device for injecting multiple settable doses according to claim 6, wherein the needle shield in, or when approaching its second position activates the dose injection mechanism for injecting the set dose.

9. An injection device for injecting multiple settable doses according to claim 1, wherein a longitudinal protrusion on the syringe body defines a distal end abutting the housing when the syringe body is in its extended position.

10. An injection device for injecting multiple settable doses according to claim 9, wherein the longitudinal protrusion defines a proximal end abutting the housing when the syringe body is in its retracted position.

\* \* \* \* \*

UNITED STATES PATENT AND TRADEMARK OFFICE
CERTIFICATE OF CORRECTION

| | |
|---|---|
| PATENT NO. | : 9,649,451 B2 |
| APPLICATION NO. | : 14/646144 |
| DATED | : May 16, 2017 |
| INVENTOR(S) | : Willem Van Der Beek et al. |

It is certified that error appears in the above-identified patent and that said Letters Patent is hereby corrected as shown below:

On the Title Page

(57) Abstract Line 1 please add an before the first instance of the phrase "injection device".

Signed and Sealed this
Fifth Day of September, 2017

Joseph Matal
*Performing the Functions and Duties of the*
*Under Secretary of Commerce for Intellectual Property and*
*Director of the United States Patent and Trademark Office*